Figure 1:
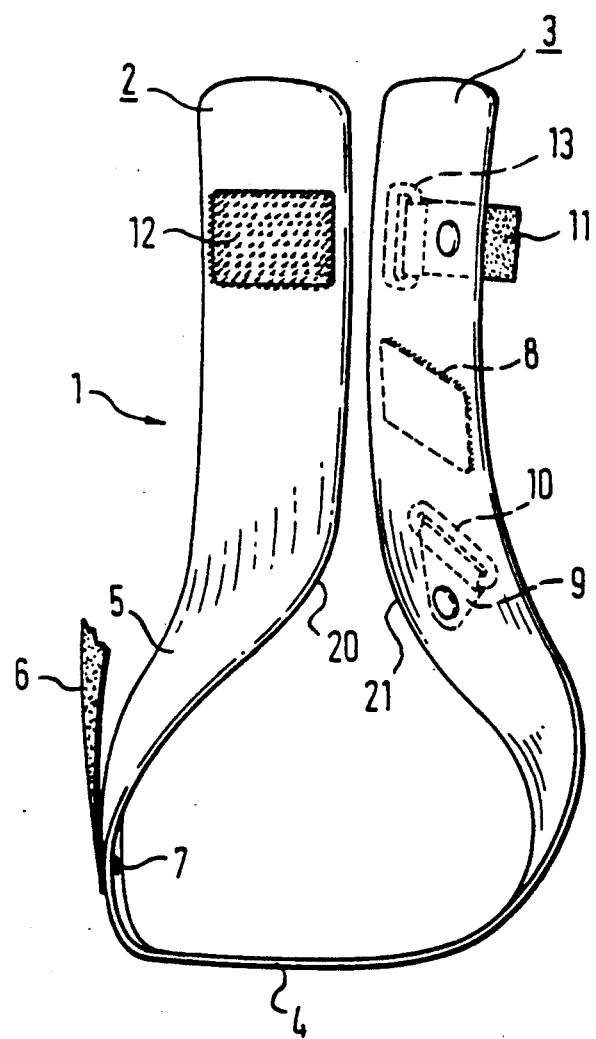

United States Patent [19]

Hess et al.

[11] Patent Number: 5,038,762
[45] Date of Patent: Aug. 13, 1991

[54] ANKLE JOINT ORTHOSIS

[75] Inventors: Heinrich Hess, Saarlouis; Wolfgang Krause, Kassel; Hans B. Bauerfeind, Kempen, all of Fed. Rep. of Germany

[73] Assignee: Bauerfeind GmbH and Company, Kempen, Fed. Rep. of Germany

[21] Appl. No.: 438,682

[22] Filed: Nov. 17, 1989

[30] Foreign Application Priority Data

Dec. 2, 1988 [DE] Fed. Rep. of Germany ....... 3840714

[51] Int. Cl.$^5$ .............................................. A61F 5/04
[52] U.S. Cl. .................................. 128/80 H; 128/80 R; 128/586
[58] Field of Search ............... 128/80 R, 81 R, 80 H, 128/80 E, 80 D, 166, 166.5, 586

[56] References Cited

U.S. PATENT DOCUMENTS

| 2,847,991 | 8/1958 | Andrews | 128/80 E |
|---|---|---|---|
| 3,506,000 | 4/1970 | Baker | 128/166 |
| 3,674,023 | 7/1972 | Mann | |
| 4,102,337 | 7/1978 | Golia | 128/80 E |
| 4,313,433 | 2/1982 | Cramer | 128/166 |
| 4,378,793 | 4/1983 | Mauldin et al. | 128/166 |
| 4,597,395 | 7/1986 | Barlow et al. | |
| 4,640,025 | 2/1987 | DeRenzo | 128/166 |
| 4,729,370 | 3/1988 | Kallassy | 128/166 |

FOREIGN PATENT DOCUMENTS

| 0154680 | 7/1984 | European Pat. Off. |
| 8700201.9 | 2/1984 | Fed. Rep. of Germany |
| 3416253A1 | 7/1985 | Fed. Rep. of Germany |
| 3435955A1 | 9/1985 | Fed. Rep. of Germany |
| 3441496C1 | 4/1986 | Fed. Rep. of Germany |
| 3537360A1 | 12/1987 | Fed. Rep. of Germany |
| 3640915A1 | 1/1988 | Fed. Rep. of Germany |

Primary Examiner—Richard J. Apley
Assistant Examiner—L. Thomas

[57] ABSTRACT

An ankle-joint orthosis which comprises a U-shaped supporting yoke consisting of flexible material, the arms of which meet in a web below the foot, extend above the malleoli and are held together in their end region by a fastening strap wrapping round the leg. The outer arm is taken upwards at the side in front of its malleolus and the inner arm is taken up opposite the outer arm, in front of the Achilles tendon. The arms are taken towards the web as far as a position in front of the heel and extend upwards towards their ends in such a manner that they rise upwards laterally beside the edges of the shinbone, substantially parallel to these. Fitted in the lower region of the arms is a supporting strap, particularly a self-gripping strap, which extends from the one arm, over the instep obliquely upwards to the other arm on which it can be fixed, engages round the Achilles tendon above the malleolus and, crossing over itself on the instep, ends in a holding member on the other arm.

6 Claims, 4 Drawing Sheets

ANKLE JOINT ORTHOSIS

The invention relates to an ankle-joint orthosis which comprises a U-shaped supporting yoke, the arms of which meet in a web underneath the foot, reach above the malleoli and are held together in their end regions by a fastening strap.

Such an orthosis is known from DE-OS 34 35 955. It consists essentially of a U-shaped supporting yoke, the arms of which extend upwards over the malleoli and are embraced in their end regions by a self-gripping strap which urges the ends of the arms against the leg. The arms meet, underneath the foot, in a web bridge which extends from the metatarsus to within the region of the heel.

It has been found in practice that although the foot, in its right-angled position, can be protected from pure lateral twisting, to some extent about an axis lying in the direction of the foot, by such orthoses, nevertheless the frequent case of slipping and bending laterally and forwards at the same time is not covered. Apart from this, the known orthosis, the stabilizing effect of which originates solely from the U-shaped supporting yoke, requires considerable bending resistance which can only be achieved by relatively strong arms.

It is the object of the invention to provide an ankle-joint orthosis which prevents bending over primarily in the direction sideways and forwards, that is to say in the direction towards a talipes equinus position. According to the invention, this is achieved in that the attachment for the outer arm is at the side in front of its malleolus and the attachment for the inner arm is opposite the outer arm, in front of the Achilles tendon, the arms extend towards the web bridge to a position in front of the heel and extend upwards towards their ends in such a manner that they rise upwards laterally beside the edges of the shinbone, substantially parallel to these, and that fitted in the lower region of the arms is a supporting strap, particularly a self-gripping strap, which extends from the one arm, over the instep obliquely upwards to the other arm to which it can be fixed, engages round the Achilles tendon above the malleolus and, crossing over itself on the instep, ends in a retaining member on the other arm.

In the region below the malleolus, the outer arm substantially follows the direction of the front outer ligament which experience has shown is exposed to particular stress on bending over sideways and forwards and which is particularly well protected by this functional-anatomical guiding of the arms. As a result of the opposition of the two arms, the ankle joint is securely gripped. Thus the arms of the supporting yoke are favourably adapted to the anatomy of the ligaments which are particularly at risk. As a result of the course of the arms towards the web as far as a position in front of the heel and towards their ends beside the edges of the shinbone, there is a line via the ends to the web which, in effect, follows the direction of the leg via the malleoli to the sole of the foot so that the pure lateral twisting of the ankle is also counteracted by this formation. Furthermore, the supporting strap embracing the ankle joint in the region of the instep and of the Achilles tendon fulfils an additional supporting function since it counteracts the actual functional pathological slipping and bending forwards and sideways as a result of the crossing over the instep. Thus there is a combination effect, with regard to supporting the ankle joint, between the supporting strap taken crosswise and the particular formation of the U-shaped supporting yoke.

The arrangement of the supporting strap may appropriately be such that this is secured by its one end to the one arm by adhesion, riveting or the like, is pulled by its other end in the form of a loop through an adjusting ring secured to the other arm and is secured to a self-gripping surface of the supporting strap by bending over, the fixing to the other arm being effected by means of a self-gripping fastener.

Thus when the supporting strap is applied, a location of the two arms in relation to one another results practically automatically, while taking up tensile stresses which extend both in the direction of the arms and transversely to these since the supporting strap joins the arms in the instep region by its crossing over and extends across the other arm in each case. When the supporting strap is applied, it is fixed to the other arm in question for which purpose a self-gripping surface provided on the arm serves in particular.

It has proved favourably both for the application of the ankle-joint orthosis and for its medicinal effect to provide the attachment point for the one end of the supporting strap on the outer arm, that of the other end on the inner arm and to provide the adjusting ring likewise on the inner arm.

The fastening strap may appropriately be used to hold the two ends of the arms at a desired distance apart. For this purpose, a self-gripping strap is fitted to one end of the one arm as a fastening strap which extends in the direction towards the other arm and, traversing this, holds it at the desired distance from the first arm by means of a self-gripping surface. When the self-gripping strap acting as a fastening strap is applied, during which the self-gripping strap is wrapped round the leg, this strap, starting from its attachment point at the end of the one arm, traverses the other arm during which it hooks onto the self-gripping surface provided at this point as a result of which, a defined spacing between the two ends of the arms results through the application of the self-gripping strap.

One embodiment of the invention is illustrated in the Figures.

Figure 2:
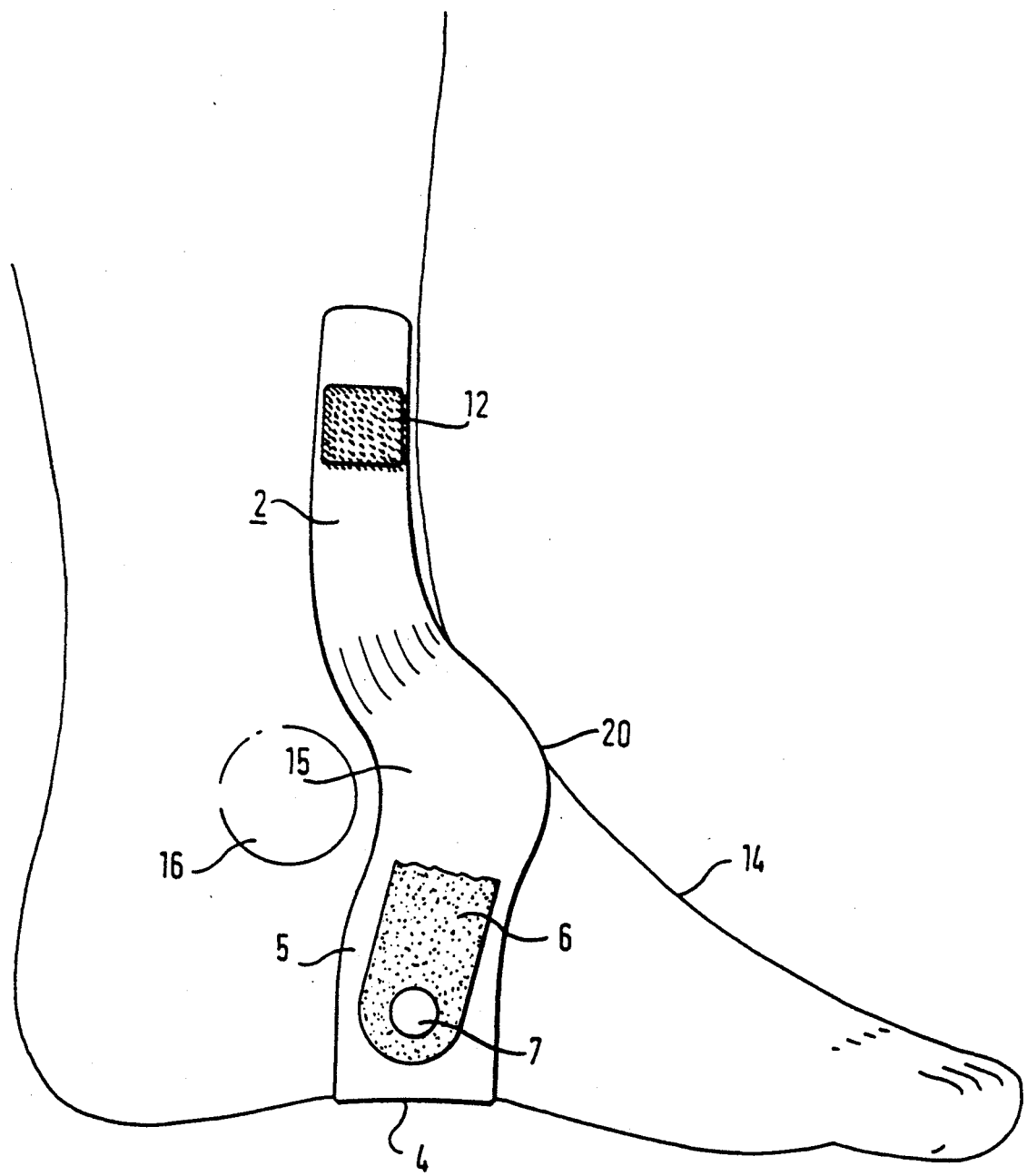
Figure 3:
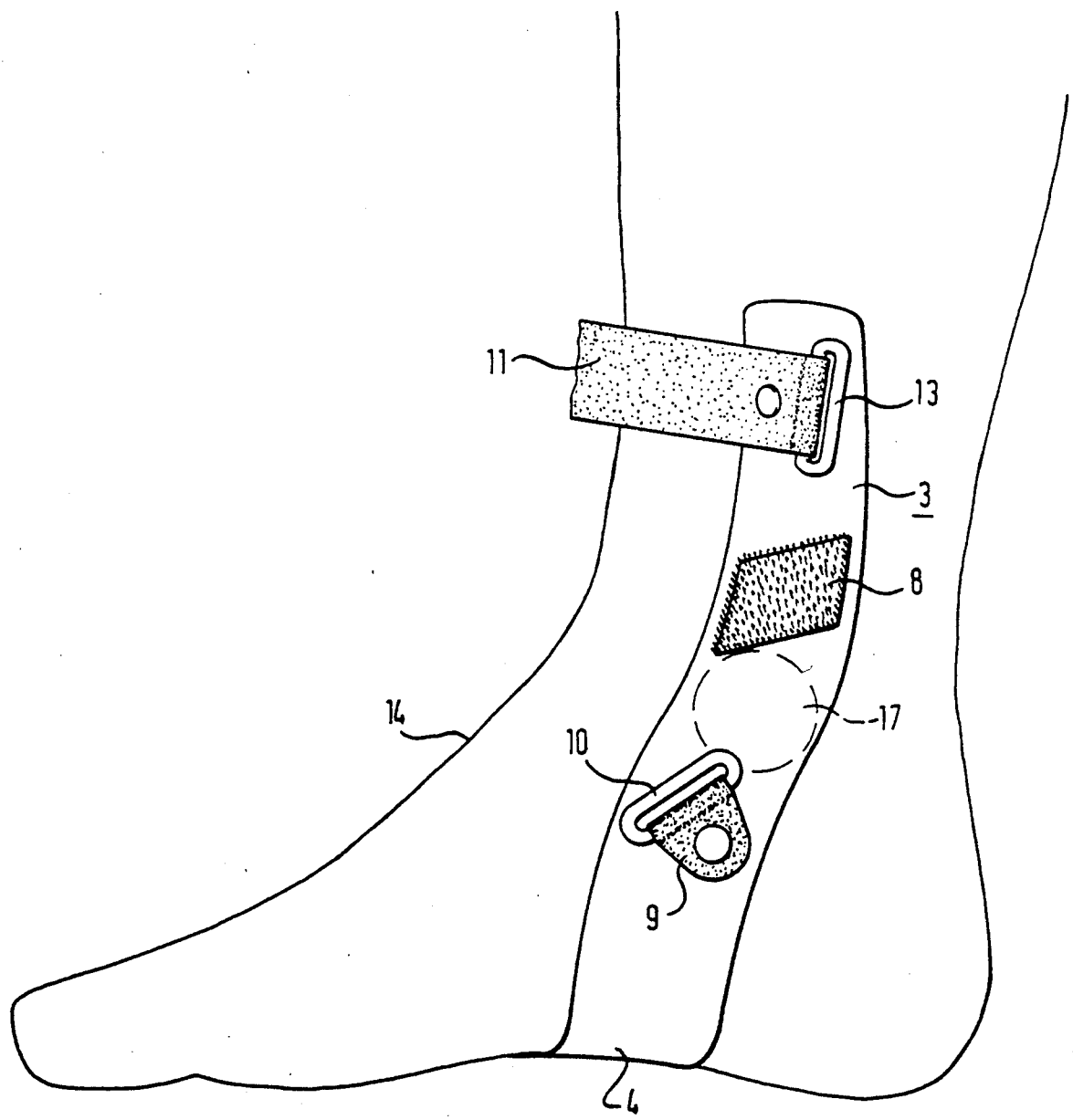
Figure 4:
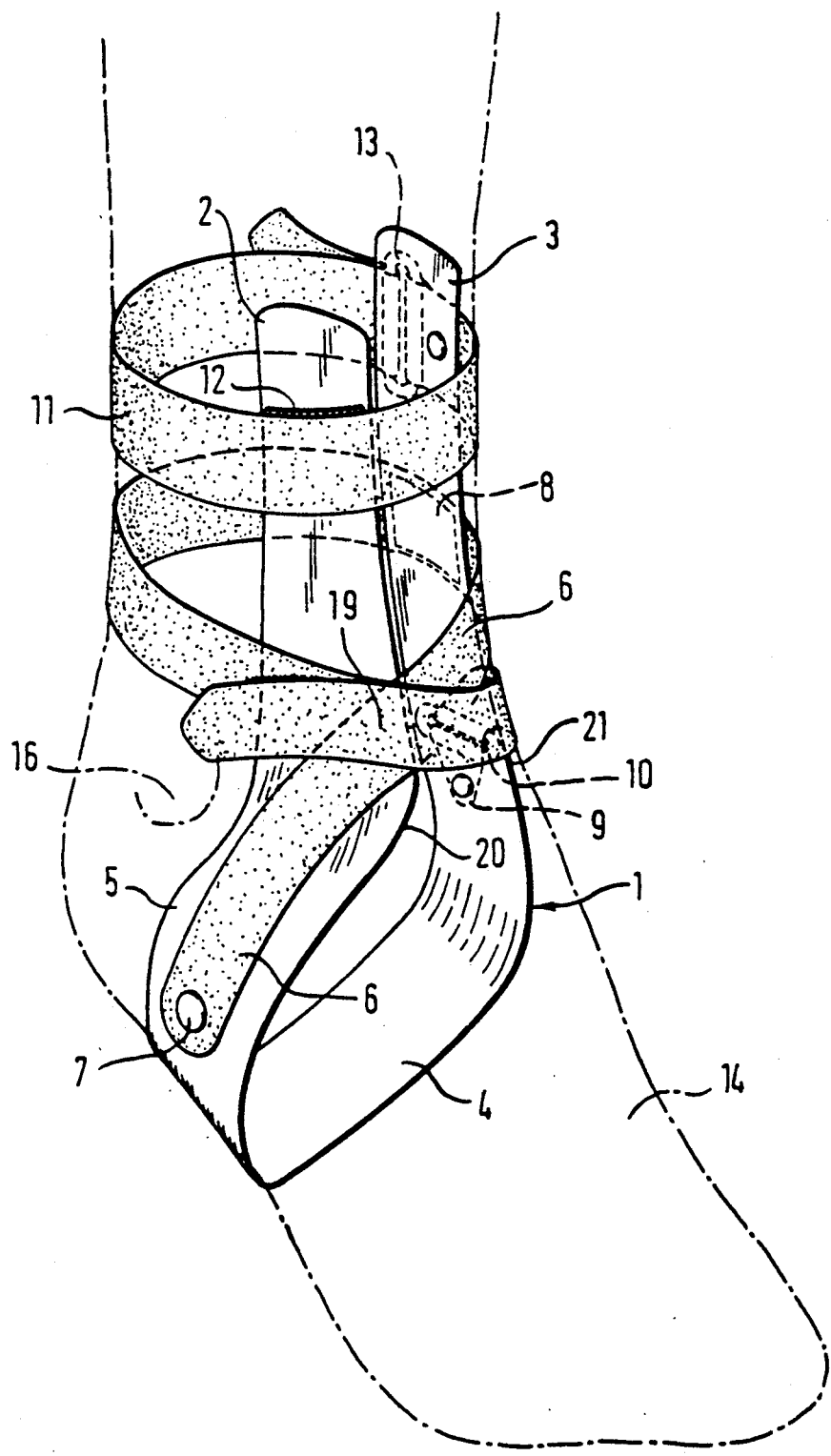

FIG. 1 shows a view of the ankle-joint orthosis seen from the toe side of a right foot, FIG. 2 shows the same orthosis on the foot, seen from the outside, FIG. 3 shows the same orthosis on the foot, seen from the inside, FIG. 4 shows the same orthosis, on the foot, illustrated in perspective, seen from the toe side.

The ankle-joint orthosis illustrated in FIG. 1 comprises the U-shaped supporting yoke 1 which consists of the two arms 2 and 3 and of the web 4 connecting the arms. Fitted in the lower region 5 of the arm 2 is the supporting strap consisting of the self-gripping strap 6 which is here rigidly connected to the arm 2 by the rivet 7. The self-gripping strap is shown broken away for reasons of clarity in the illustration. Provided in the region above the instep, on the arm 3, is the self-gripping surface 8 which consists of a piece of self-gripping fastener attached by adhesion. During the application of the orthosis, the self-gripping strap 6 is laid over this self-gripping surface 8 as is explained in more detail with reference to FIG. 4.

The second attachment point for the applied self-gripping strap is provided in the form of the riveted-on tongue 9 with an adjusting ring 10 secured thereto, below the self-gripping surface 8. During the application of the self-gripping strap 6, this is pulled through the adjusting ring and held by means of a self-gripping fastening, which will likewise be gone into in more detail in connection with FIG. 4.

Fitted at the upper end of the arm 3 is the one end of the fastening strap 11 which is here shown broken away for reasons of clarity in the illustration. It extends in the direction towards the other arm 2 on the end of which the self-gripping surface 12 is provided opposite the attachment point of the fastening strap 11, for example by securing a self-gripping fastener by adhesion. When the fastening strap 11, is applied, it is laid over the self-gripping surface 12 and clings firmly to this. This will be gone into in more detail below in connection with FIG. 4. The fastening strap 11 ends at its rear side in the adjusting ring 13 into which the other end of the fastening strap 11 is introduced after its application and round which it is wrapped.

The ankle-joint orthosis illustrated in FIG. 1 is illustrated in FIG. 2 seen from the side and applied to a right foot 14, actually seen from the outside of the foot 14. As can be seen, the arm 2 extends as a partial rounding 15 round the outer malleolus, indicated symbolically as a circle, 16.

In FIG. 3, the same orthosis is represented applied to the right foot 14, seen from the inside of the foot 14. The arm 3, which is visible here, extends in front of the Achilles tendon over the inner malleolus 17. Fitted to it by means of the riveted-on tongue 9 is the adjusting ring 10 which serves to secure the relevant end of the self-gripping strap 6 (see FIg. 1). Provided above the adjusting ring is the self-gripping surface 8, the function of which has already been gone into in connection with FIGS. 1 and 2. Riveted on in the region of the upper end of the arm 3 is the one end of the fastening strap 11 which is here shown broken away for reasons of clarity in the illustration. The fastening strap 11 ends towards the rear in the adjusting ring 13 into which the fastening strap 11 is pulled after wrapping round the leg.

With regard to FIGS. 2 and 3, it may also be pointed out that these also show the web 4 which here lies directly in front of the region of the heel of the foot 14.

In FIG. 4, the ankle-joint orthosis 1 applied to a right foot 14 is represented in partial repetition of the illustration in FIG. 1.

Starting from the attachment point with the rivet 7, the self-gripping strap 6 is taken forward over the instep of the foot 14 and in the course of this, crossing the arm 3 in the region above the instep, reaches the self-gripping surface 8 by which the self-gripping strap 6 is held. The self-gripping strap 6 is then wrapped round the foot 14 towards the back above the malleolus 16 (17 not visible) round the Achilles tendon. The self-gripping strap 6 is then taken over the instep via the crossing point 19 to the adjusting ring 10 through which it is looped and is held by being folded over backwards and pressed against the underlying portion of the self-gripping strap 6. A self-gripping fastener provided at this point likewise serves this purpose.

Thus a supporting of the ankle joint results from several points of view. On the one hand, the arms 2 and 3 extend, as can be seen in FIGS. 2 and 3, opposite one another, in the longitudinal direction of the leg, laterally beside the edges of the shinbone. In effect, there is continuous supporting, extending substantially in the longitudinal direction of the leg, by the arms 2 and 3 so that a pure lateral twisting of the ankle is practically avoided completely, as explained above. In addition, the partial rounding 15 leads to the important effect that the transition region 20 over the instep extends obliquely inwards and upwards, while the outer region 20 extends substantially in the direction of the front outer ligaments and is thus able to take up any overloading falling on these. At the same time, this capacity to take up such stresses is decisively reinforced by the self-gripping strap 6 which on the one hand follows the direction of this region and after wrapping round the foot reaches the opposite region by crossing over itself and there takes up any tensile stresses which occur. Finally, the crossed wrapping round the foot by the self-gripping strap 6 causes a firm connection between the foot 14 and the arms 2 and 3.

The fastening strap fitted to the ends of the arms 2 and 3 is utilized, as FIG. 4 clearly shows, to hold the ends of the arms 2 and 3 with the desired spacing apart, which ultimately amounts to the fact that the two arms 2 and 3 extend substantially parallel to one another at the side of the edges of the shinbone and are held in this position. The fastening strap 11, which may appropriately likewise be constructed in the form of a self-gripping strap and which is secured, facing in the direction of the arm 2, to the arm 3, is laid over the arm 2 and in the course of this presses against the self-gripping surface 12 by which the fastening strap 11 is then held. As a result of this, there is a defined spacing between the two ends of the arms 2 and 3. The fastening strap 11 is then wrapped round the leg, pulled into the adjusting ring 13 and bent over backwards, in the course of which it is pressed against the subjacent region of the fastening strap 11 and clings to this by means of a self-gripping fastener.

We claim:

1. An ankle-joint orthosis which comprises a U-shaped supporting yoke (1) consisting of flexible material, the arms (2,3) of which meet in a bridge (4) underneath the foot (14), extend above the ankle (16,17) and are held together in their end region by a fastening strap (11) wrapped round the leg, characterised in that the outer arm (2) is taken up at the side in front of its malleolus (16) and the inner arm (3) is taken up opposite the outer arm (2) in front of the Achilles tendon, the arms (2,3) extend from the bridge (4) as far as a portion in front of the heel and extend upwards towards their ends in such a manner that they rise upwards laterally beside the edges of the shinbone substantially parallel to these, and that, in the lower region of the arms (2,3), a supporting strap (6), particularly a self-gripping strap, is fitted which extends from the one art (2) over the instep obliquely upwards to the other arm (3) which it engages and extends round the Achilles tendon above the malleoli (16,17) and, crossing over itself on the instep, ends in a retaining member (10) on the other arm (3).

2. An ankle joint orthosis according to claim 1, characterized in that the supporting strap (6) is secured by its one end to the one arm (2) by adhesion (7) is pulled by its other end, in the form of a loop, through an adjusting ring (10) secured to the other arm (3), and is secured to a self-gripping surface of the supporting strap (6) by bending over, the fixing to the other arm (3) being effected by means of a self-gripping fastener (8).

3. An ankle-joint orthosis according to claim 1, characterized in that an attachment point (7) for the one end of the supporting strap (6) is provided on the outer arm (2) and the other end of the supporting strap (6) is fixed (8) to the inner arm (3), and the adjusting ring (10) is likewise provided on the inner arm (3).

4. An ankle-joint orthosis according to claim 1, characterized in that fitted to the end of the one arm (9) as a fastening strap (11) is a self-gripping strap which extends towards the other arm (2) and, traversing this, holds it at the desired distance from the first arm (3) by means of a self-gripping surface (12).

5. An ankle joint orthosis according to claim 2, characterized in that an attachment point (7) for the one end of the supporting strap (6) is provided on the outer arm (2) and the other end of the supporting strap (6) is fixed (8) to the inner arm (3), and the adjusting ring (10) is likewise provided on the inner arm (3).

6. An ankle joint orthosis according to claim 1, characterized in that the supporting strap (6) is secured by its one end to the one arm (2) by riveting, is pulled by its other end, in the form of a loop, through an adjustable ring (10) secured to the other arm (3), and is secured to a self-gripping surface of the supporting strap (6) by bending over, the fixing to the other arm (3) being effected by means of a self-gripping fastener (8).

* * * * *